United States Patent
Somers

(10) Patent No.: US 7,489,142 B2
(45) Date of Patent: Feb. 10, 2009

(54) PROXIMITY SENSOR FOR X-RAY APPARATUS

(75) Inventor: Petrus Lambertus Maria Somers, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/573,909

(22) PCT Filed: Aug. 25, 2005

(86) PCT No.: PCT/IB2005/052791

§ 371 (c)(1),
(2), (4) Date: Feb. 19, 2007

(87) PCT Pub. No.: WO2006/025000

PCT Pub. Date: Mar. 9, 2006

(65) Prior Publication Data

US 2007/0242805 A1    Oct. 18, 2007

(30) Foreign Application Priority Data

Aug. 31, 2004 (EP) .................................. 04104156
Jan. 20, 2005 (EP) .................................. 05100329

(51) Int. Cl.
*G01R 27/26* (2006.01)

(52) U.S. Cl. ................... 324/661; 324/677; 324/690; 307/116; 341/33; 280/735

(58) Field of Classification Search .................. 324/661
See application file for complete search history.

(56) References Cited

U.S. PATENT DOCUMENTS

| | | | | |
|---|---|---|---|---|
| 4,107,555 A * | 8/1978 | Haas et al. | ................... | 307/116 |
| 4,486,811 A | 12/1984 | Kamiya et al. | | |
| 5,651,044 A * | 7/1997 | Klotz et al. | ................... | 378/117 |
| 5,726,581 A | 3/1998 | Vranish | | |
| 5,883,935 A | 3/1999 | Habraken et al. | | |
| 6,593,755 B1 * | 7/2003 | Rosengren | ................... | 324/677 |
| 6,724,324 B1 * | 4/2004 | Lambert | ...................... | 341/33 |
| 2001/0031039 A1 | 10/2001 | Habraken | | |
| 2003/0057968 A1 * | 3/2003 | Wang et al. | .................. | 324/690 |
| 2003/0061524 A1 * | 3/2003 | Casebolt et al. | ............. | 713/300 |

(Continued)

FOREIGN PATENT DOCUMENTS

EP        334531 A1       9/1989

(Continued)

*Primary Examiner*—Timothy J Dole
*Assistant Examiner*—Benjamin M Baldridge

(57) ABSTRACT

A capacitive proximity sensor for use in object and position sensing and/or position control in respect of a swing arm of a medical imaging system. The sensor comprises, within a cover (18), an emitter electrode (10) and a sense electrode (9) both of which are formed by spraying or otherwise coating or painting a layer of conductive material on the inner surface of the cover (18). A carrier plate (30) is mounted within the cover (18), at a distance therefrom, on which are provided an active guard electrode (13) in respect of the sense electrode (9) and a grounded shield member (15) in respect of the emitter electrode (10). As there is virtually no gap between the sense electrode (9) and the cover (18), the sensor is less sensitive to the effects of material changes caused by environmental changes in temperature and/or humidity, for example.

19 Claims, 5 Drawing Sheets

U.S. PATENT DOCUMENTS

| | | | |
|---|---|---|---|
| 2003/0080744 A1* | 5/2003 | Goldfine et al. | 324/345 |
| 2004/0017210 A1 | 1/2004 | Johnson et al. | |
| 2005/0253513 A1* | 11/2005 | Park et al. | 313/581 |
| 2005/0270752 A1* | 12/2005 | Credelle et al. | 361/736 |
| 2005/0275202 A1* | 12/2005 | Wato et al. | 280/735 |
| 2005/0275385 A1* | 12/2005 | Hosking | 320/166 |

FOREIGN PATENT DOCUMENTS

| | | |
|---|---|---|
| EP | 1164240 A1 | 12/2001 |
| WO | 0044018 A | 7/2000 |

* cited by examiner

PROXIMITY SENSOR FOR X-RAY APPARATUS

This invention relates generally to a capacitive proximity sensor for use in, for example, preventing collisions of a motorised swing arm with nearby objects or people.

Referring to FIGS. 1 and 2 of the drawings, a typical X-ray system comprises a swing arm (C-arc or G-arc) 1 supported proximal a patient table 2 by a robotic arm 3. Housed within the swing arm 1, there is provided an X-ray tube 4 and an X-ray detector 5, the X-ray detector 5 being arranged and configured to receive X-rays 6 which have passed through a patient 7 and generate an electrical signal representative of the intensity distribution thereof.

By moving the swing arm 1, the X-ray tube 4 and detector 5 can be placed at any desired location and orientation relative to the patient 7. Movement of the swing arm 1 is driven by one or more motors (not shown), and in order to protect the patient, the operator and/or other objects from collisions with the swing arm, proximity sensors are placed at critical locations A, B, C and D on the arc of the swing arm 1.

A proximity sensor which is commonly used for this application is known as a capacitive proximity sensor that is able to sense any object or person that is capacitive relative to ground and/or can be statically charged. Capacitive proximity sensors use the face or surface of the sensor as one plate of a capacitor, and the surface of a conductive or dielectric target object as the other. The capacitance varies inversely with the distance between capacitor plates in this arrangement, and a certain value can be set to trigger target detection. The sensing principle is based on the measurement of a change in electric field profile. Thus, if the sensor detects an object, the output voltage will change. A control system is employed to control the speed of the swing arm drive motor if the output voltage drops below a certain level, so as to reduce the motor speed and, eventually, stop it to avoid a collision. Such a control system is known from, and described in, for example, U.S. Patent Application Publication No. US2004/0017210 A1.

Referring to FIG. 3 of the drawings, in more detail, a known capacitive proximity sensor arrangement comprises a 100 kHz sine oscillator 8, which is capacitively coupled to a sense or "receiver" electrode 9, via an emitter electrode 10 and an electric field (denoted by field lines 11) is created which travels from the emitter 10 to the receiver 9. The receiver 9 is connected to an amplifier 12 having a very high input impedance ("approaching infinity") and a very low output impedance. The gain of the amplifier 12 is approximately unity. The receiver electrode 9 is connected to the input of the amplifier 12 and the output of the amplifier 12 is used to drive a guard electrode 13. Thus, the guard electrode 13 is driven by a signal identical to, but electrically isolated from, the signal imposed on the receiver electrode 9, and the capacitance between the guard electrode 13 and ground cancels the capacitance between the receiver electrode 9 and ground, thereby enhancing the sensitivity of the sensor. The guard electrode 13 shields all parts of the receiver electrode 9 which are not facing a potential obstacle, and this guarding method is known as "active guarding" and, by connecting the output of the 1× amplifier to the guard electrode 13, the receiver electrode 9 "sees" its own potential in the direction of the guard electrode 13, so the space surrounding this area is potential free and no electric field will result. A grounded shield 15 is provided in respect of the sides of the emitter electrode 10 not facing a potential obstacle 14. The output of the amplifier 12 is fed to signal conditioning means 16, the output 17 of which is fed to a processing system (not shown).

When there is no grounding object 14 in the proximity of the sensor, the total capacitive coupling between the emitter and receiver electrodes 9, 10 will "land" on the receiver electrode 9, and its potential will rise to a maximum. The measured potential is rectified and sent as a buffered DC voltage to the processing system. When a grounded object 14 approaches the electrode structures, a part of the potential present on the receiver electrode 9 is drawn away to ground, thereby resulting in a decrease in sense potential, and a corresponding decrease in DC output voltage when a grounded object 14 enters the measuring volume. In order to determine the precise location, orientation and direction of travel of a potential obstacle, several sensors are mounted at key locations A, B, C and D within the protective cover 18 of a swing arm. Conventionally, the guard electrode 13, the emitter electrode 10, the receiver electrode 9 and the grounded shield 15 are combined on a single printed circuit board, which is then glued inside the cover 18.

Thus, referring to FIGS. 4a and 4b of the drawings, conventionally, the receiver electrode 9 and the emitter electrode 10 are provided on one side of a carrier plate 30, facing the sensor cover 18, and the respective active guard electrode 13 and grounded shield 15 are typically provided on the opposite side of the carrier plate 30. The carrier plate 30, thus configured, is then mounted within the swing arm behind the sensor cover 18, such that there is a gap 32 between the receiver electrode 9 and the sensor cover 18. In use, the arrangement defines the sensitive object detection area 34 shown in FIG. 4a.

However, this construction makes the sensor especially sensitive to very small local changes, such as very small changes in distance between the sensor and the cover caused by temperature and humidity changes in the surrounding environment. Since the system is unable to distinguish this effect from the detection of an object or identification of a faulty sensor, the system can be caused to slow down unnecessarily, at least from 25° to 8° in practical systems, or even down to 0° per second, and a repeating beep is often present to indicate that the sensor cannot be relied upon. Depending upon the specific circumstances, it is considered that in the X-ray imaging field, at least one additional patient per day could be treated if the system could be prevented from slowing down unnecessarily in this manner.

It is therefore an object of the present invention to provide a proximity sensor having increased stability in the presence of changes in ambient and environmental conditions.

In accordance with the present invention, there is provided a proximity sensor comprising within a cover an emitter electrode, a sense electrode and means for generating an electric field from said emitter electrode to said sense electrode, the sensor further comprising a cover, wherein said sense electrode comprises a layer of conductive material provided directly on an inner surface of said cover.

Also in accordance with the present invention, there is a method of manufacturing a proximity sensor comprising providing, within a cover, an emitter electrode and means for generating an electric field from said emitter electrode, the method further comprising forming a sense electrode by providing a layer of conductive material directly on an inner surface of said cover.

Thus, the present invention provides a proximity sensor construction that is more stable and independent of humidity and temperature changes, relative to prior art sensors. Because there is virtually no gap between the sense electrode and the cover, the sensitivity of the sensor to small changes in distance between the sense electrode and the cover due to changes in $\epsilon_r$ caused by changes in humidity and temperature is significantly reduced, because even if the $\epsilon_r$ of the sensor cover changes with changing environmental conditions, there is no effect on the voltage output of the sensor because no distance changes between the sense electrode and the cover can take place.

An additional benefit of the construction defined above is that the electrodes can follow the curves of the sensor cover better, which more freedom in the cover design process.

The present invention extends to a swing arm for an imaging system, said swing arm comprising a radiation source and detector, and further comprising one or more proximity sensors as defined above.

The present invention extends further to an imaging system, comprising a swing arm as defined above, motive means for moving said swing arm to a desired position relative to a subject to be imaged, and means for controlling said motive means according to the output of said one or more sensors.

The conductive layer may, for example, comprise a layer of conductive adhesive material, such as tape, but more preferably comprises a conductive material which is vaporised/metallised or sprayed, or otherwise painted or coated, directly on the inner surface of the sensor cover. Spraycoating is a very fast, well known process in many fields, and results in quicker prototyping and shorter development time which, in turn, enables customer feedback integration in new designs relatively easily.

It will be appreciated that, in a preferred embodiment, the emitter electrode also comprises a layer of conductive material provided directly on the inner surface of the cover. A carrier plate is preferably mounted within the cover at a distance from the sense electrode and the emitter electrode provided on the inner surface of the cover, wherein an active guard electrode is provided in respect of the sense electrode on a surface of the carrier plate facing the cover and a grounded shield member is provided in respect of the emitter electrode on said surface of said carrier plate facing the inner surface of the cover.

These and other aspects of the present invention will be apparent from, and elucidated with reference to, the embodiment described herein.

An embodiment of the present invention will now be described by way of example only and with reference to the accompanying drawings, in which.

Figure 4A:
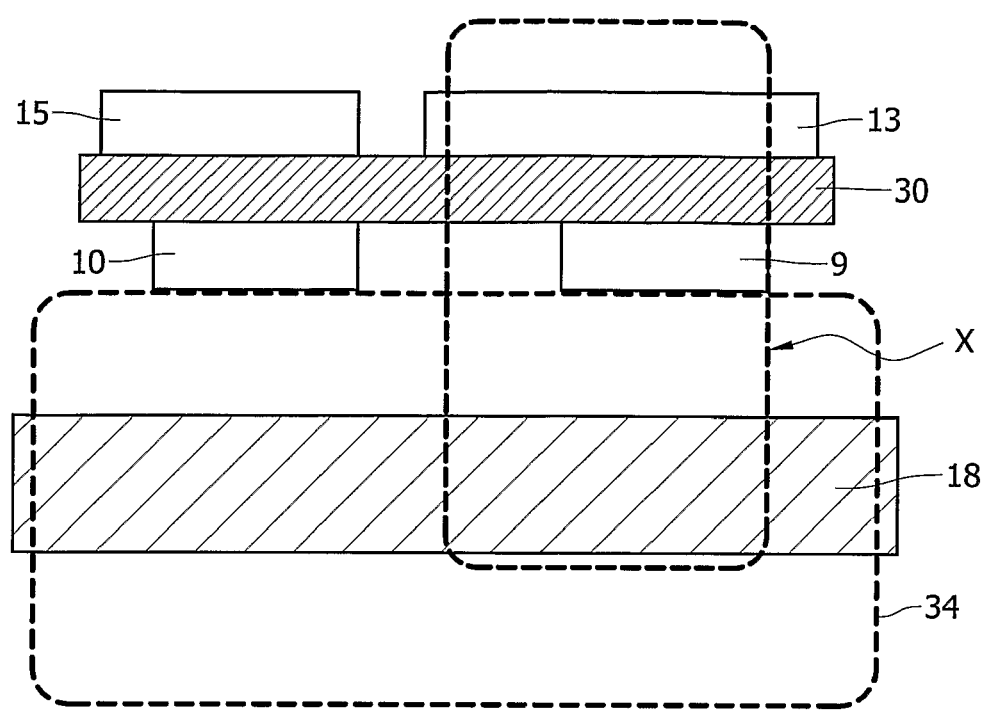
Figure 4B:
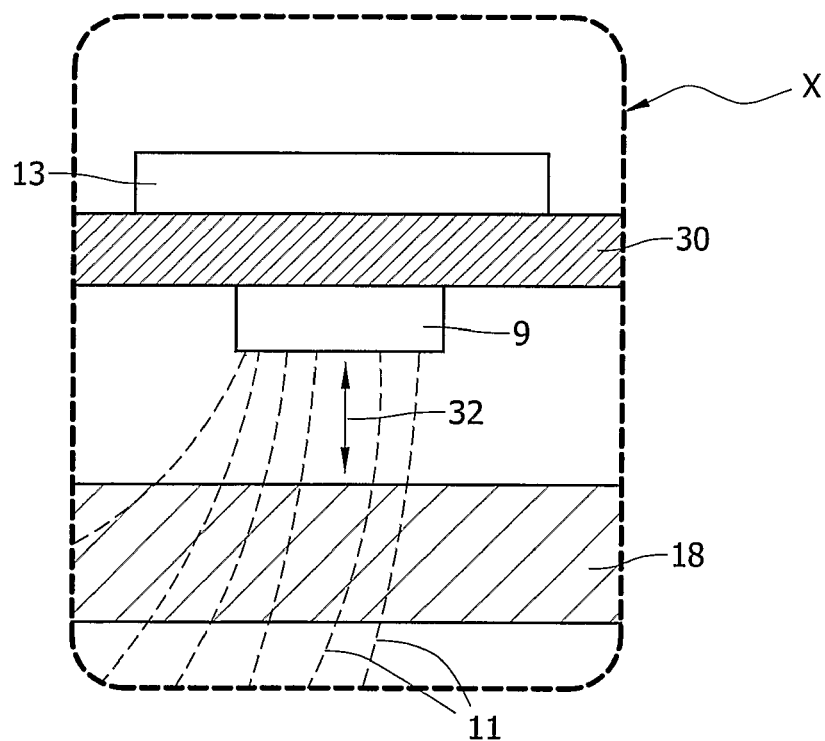
Figure 5A:
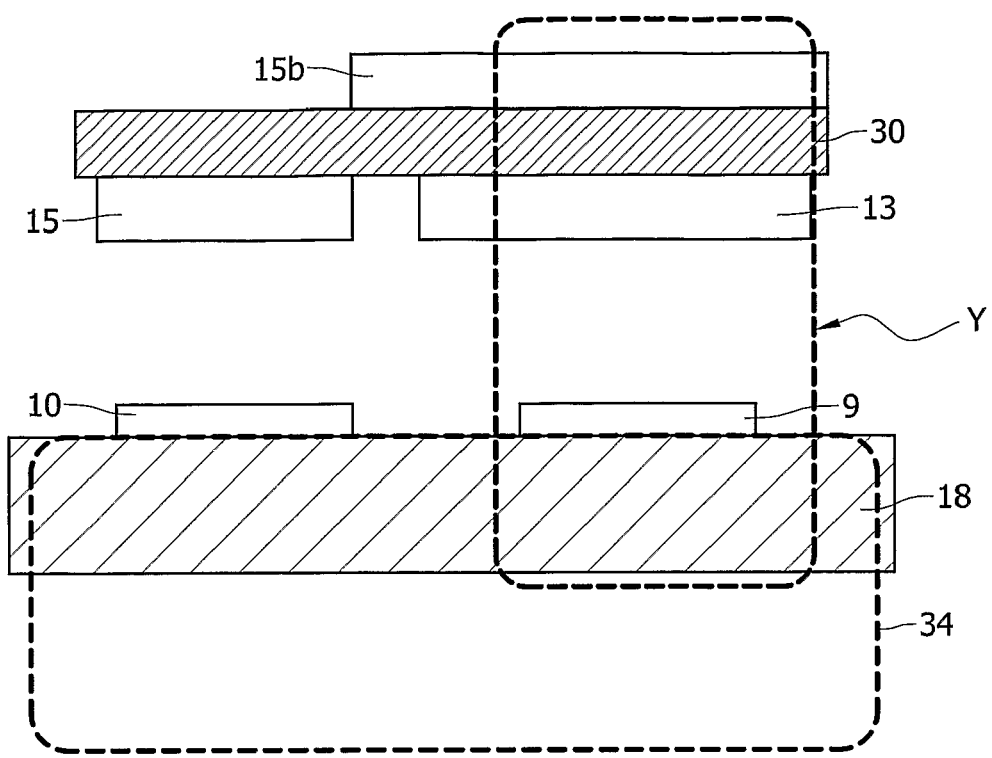
Figure 5B:
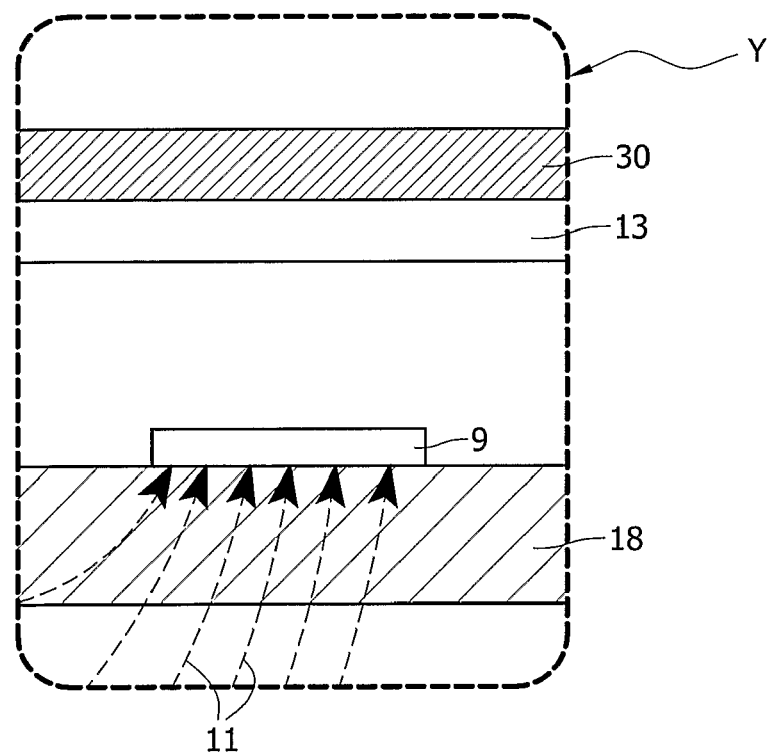
Figure 6A:
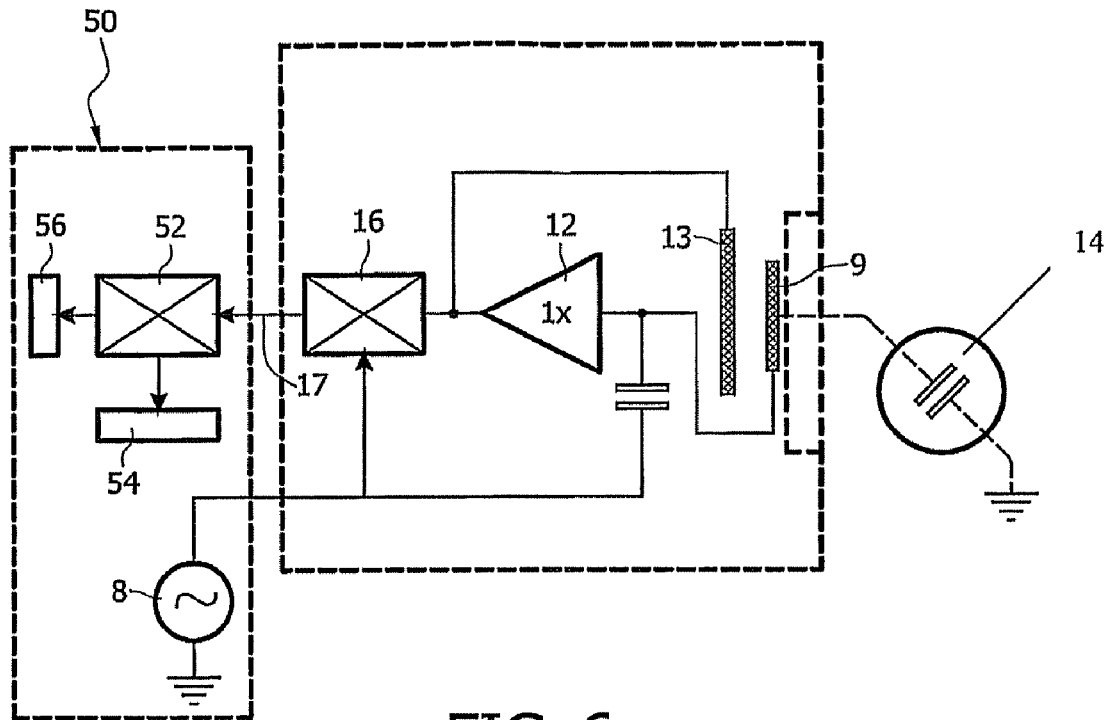
Figure 6B:
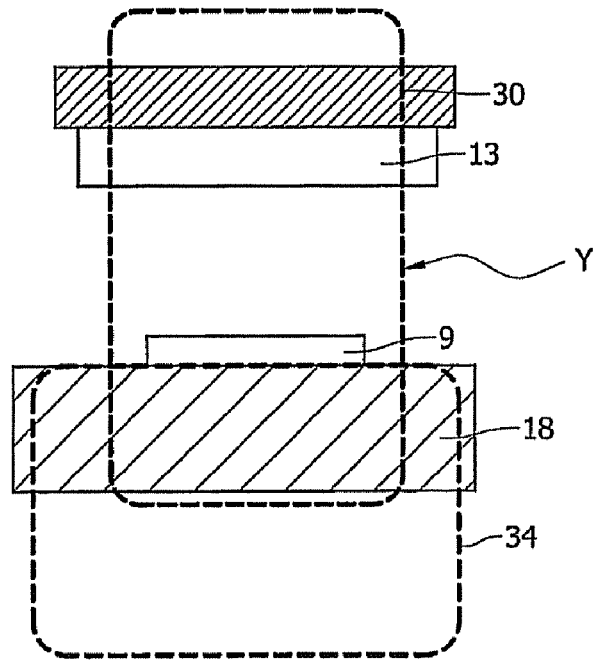

FIG. 4*a* is a schematic cross-sectional view illustrating the construction of a conventional proximity sensor;

FIG. 4*b* is a schematic cross-sectional view of detail X of FIG. 4*a*;

FIG. 5*a* is a schematic cross-sectional view illustrating the construction of a proximity sensor according to a first exemplary embodiment of the present invention;

FIG. 5*b* is a schematic cross-sectional view of detail Y of FIG. 5*a*;

FIG. 6*a* is a schematic circuit diagram illustrating the construction of a proximity sensor system according to a second exemplary embodiment of the present invention; and FIG. 6*b* is a schematic cross-sectional view (corresponding to detail Y of FIG. 5*b*) of the proximity sensor of the system of FIG. 6*b*.

Referring briefly back to the sensor construction illustrated in FIGS. 4*a* and 4*b* of the drawings, because of the gap 32 between the sense and emitter electrodes 9, 10 and the sensor cover 18, the sensor cover 18 is "seen" by the sense electrode 9 as an object at a certain distance therefrom. If the gap 32 changes between the sense and emitter electrodes 9, 10 and the sensor cover 18, the sensor effectively "sees" a changing objects. Because the sensor cover 18 is so close to the sense electrode 9, where its sensitivity is highest, even minute changes in the gap 32 will have a significant effect on the output voltage of the sensor, to the extent that changes caused by changes in material characteristics (expansion and contraction) of the sensor cover 18 with changes in environmental conditions (humidity and temperature) can have a significant effect on the output voltage of the sensor.

This problem is overcome in accordance with the present invention by forming the sense and emitter electrodes 9, 10 directly on the inner surface of the sensor cover 18. Thus, referring to FIGS. 5*a* and 5*b* of the drawings, a proximity sensor according to an exemplary embodiment of the present invention comprises a carrier plate 30 mounted within a sensor cover 18 at a distance therefrom. A sense electrode 9 and emitter electrode 10 are provided directly on the inner surface of the sensor cover 18 by forming respective layers of conductive material thereon. This may be achieved, for example, by spraying, vaporising metallisation, or otherwise coating or painting, the surface of the cover plate 18 with a conductive paint or epoxy, or by using conductive adhesive tape.

Figure 1:
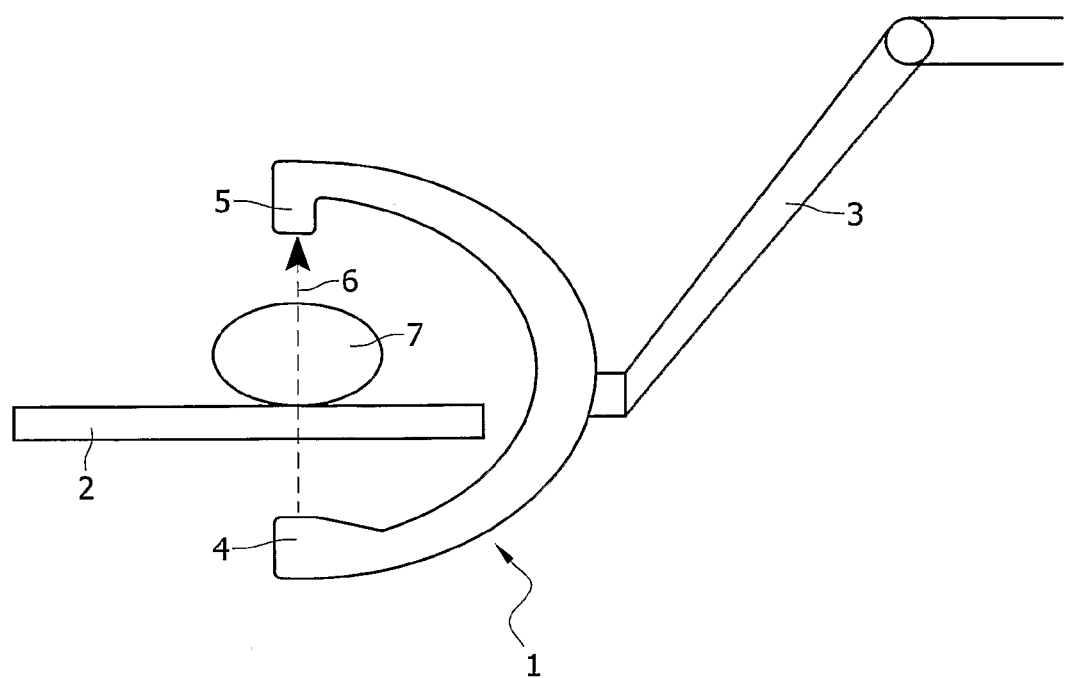
FIG. 1 is a schematic side view of an X-ray swing arm.
Figure 2:
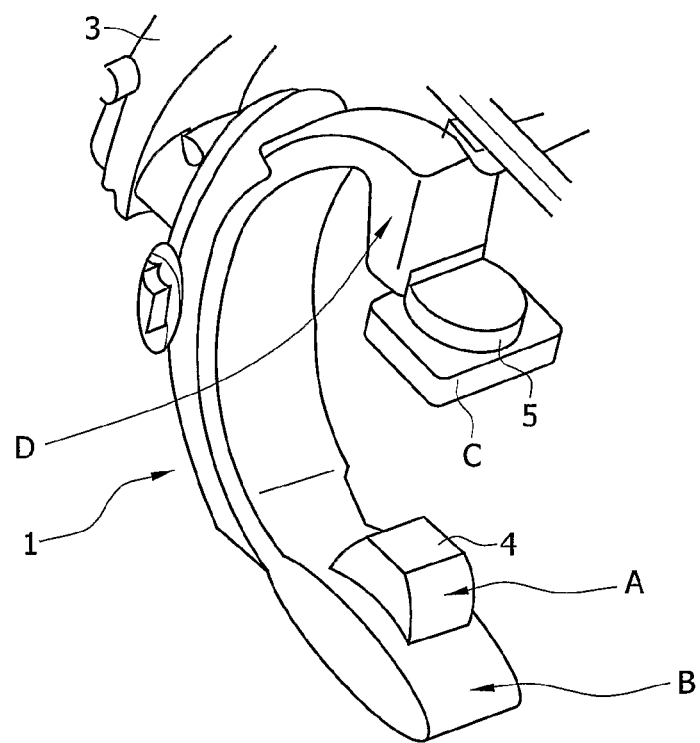
FIG. 2 is a perspective view of an X-ray swing arm.
Figure 3:
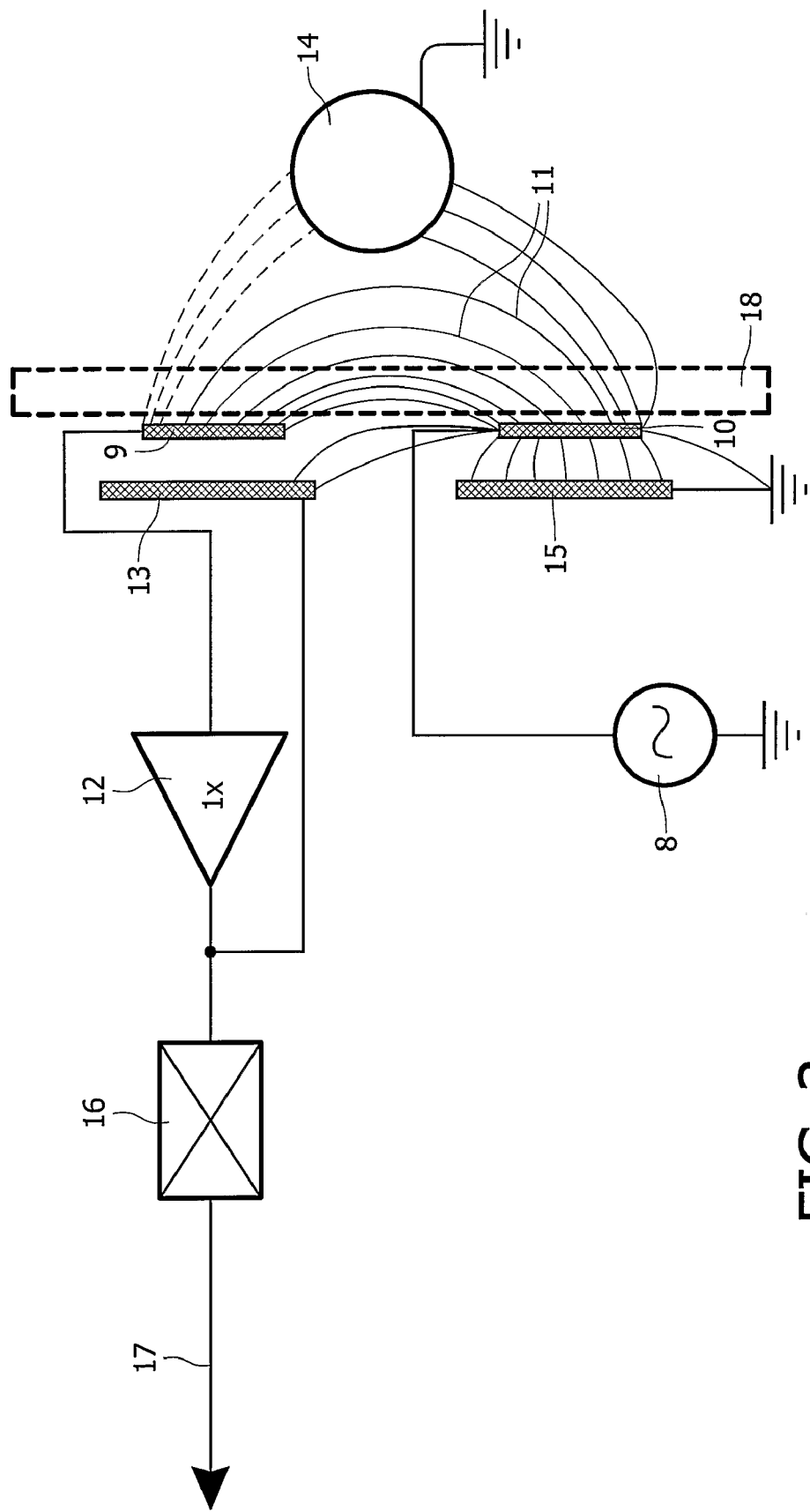
FIG. 3 is a schematic diagram illustrating the principle of construction of a capacitive proximity sensor according to the prior art.

An active guard electrode 13 is provided in respect of the sense electrode 9, in a conventional manner for preventing sensor sensitivity in the unwanted direction (i.e. away from where an object required to be sensed might be located), but in this case, the active guard electrode 13 is provided on the surface of carrier plate 30 facing the sensor cover 18. Similarly, a grounded shield or screen 15 is provided in respect of the emitter electrode 10, in a conventional manner for preventing radiation of electric field lines 11 in the above-mentioned unwanted direction, but again in this case the grounded shield 15 is provided on the surface of the carrier plate 18 facing the sensor cover 18. In order to create a constant capacitance between the active guard 13 and ground, a grounded shield 15*b* can be provided on the carrier plate 30. The load for the driver 12 (see FIG. 3) is now constant and does not vary due to earthed components on that side of the sensor.

In the arrangement of FIGS. 5*a* and *b*, the signal (denoted by the electric field lines 11) passes through the cover 18 twice (i.e. going out from the emitter 10 and coming back in to the receiver 9). Thus, the above-mentioned material changes in the cover 18 can influence the field lines 11 twice, i.e. the field lines 11 between the sense electrode 9 and the object (14-Figure) are affected and also the field lines 11 between the emitter 10 and the object 14.

Referring to FIG. 6*a* of the drawings, a more temperature/humidity stable arrangement is illustrated, based on just a receiver electrode 9 (with the emitter electrode omitted). The required emitter signal is now capacitively (or, in any event, by some impedance) coupled to the receiver electrode 9 on the carrier plate (30-referring additionally to FIG. 6*b* of the drawings) by means of a temperature stable capacitor. The output 17 from the amplifier 12 and signal conditioning means 16 is fed to a processing system 50, comprising further signal conditioning means 52, a digital-to-analog converter (DAC) 54 and an analog-to-digital converter (ADC) 56.

If an object 14 (which presents a capacitive load to ground) approaches the receiver electrode 9, the input voltage will be divided between the two capacitors) i.e. the capacitive coupling between the oscillator 8 and the receiver electrode 9 and the capacitive load presented by the object 14), which causes a corresponding reduction in the sensor output voltage. Thus, because only the receiver electrode 9 is present in the design and due to the capacitive coupling on the carrier plate 30, the field lines from the emitter 8 do not pass through the sensor cover 18, such that the material characteristics of the cover 18 (and changes therein caused by changes in temperature/humidity) have no influence on the emitted electric field lines (only on those received by the receiver electrode 9).

The principle of the present invention works in this case, as before. The sense electrode 9 is formed directly on the inner surface of the sensor cover 18 by forming a layer of conductive material thereon. Once again, this may be achieved, for example, by spraying, vaporising, metallization, or otherwise coating the surface of the cover plate 18 with a conductive paint, epoxy or other conductive material, or by using conductive adhesive tape. An active guard electrode 13 is provided in respect of the sense electrode 9, in a conventional manner for preventing sensor sensitivity in an unwanted direction (i.e. away from where an object required to be sensed might be located), and this active guard electrode 13 is again provided on the surface of the carrier plate 30 facing the sensor cover 18. The sensitive object detection area is once again denoted by reference numeral 34.

The present invention is suitable for use in all fields, including medical fields, where the provision of a distance sensor is considered advisable or necessary, for preventing patient, operator or object collisions during system movements, and/or, for example, locating the general position of a patient or other subject.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A proximity sensor comprising: a cover, an emitter electrode, a sense electrode and means for generating an electric field from said emitter electrode to said sense electrode, wherein the emitter electrode and the sense electrode are at least substantially enclosed by the cover, wherein said sense electrode comprises a first layer of conductive material provided directly on an inner surface of said cover, wherein said emitter electrode comprises a second layer of conductive material provided directly on the cover, wherein a carrier plate is mounted at a distance from the sense electrode and the emitter electrode, wherein the carrier plate is at least substantially enclosed by the cover, wherein an active guard electrode is provided in respect of the sense electrode on a surface of the carrier plate facing the cover and a grounded shield member is provided in respect of the emitter electrode on said surface of said carrier plate facing the cover.

2. A sensor according to claim 1, wherein at least one of said first and second layers of conductive material comprises a layer of conductive adhesive material tape.

3. A sensor according to claim 1, wherein at least one of said first and second layers of conductive material comprises a conductive material which is sprayed directly on said inner surface of the cover.

4. A sensor according to claim 1, wherein a grounding shield is connected to the carrier plate on a surface opposite to said surface having said active guard electrode.

5. A sensor according to claim 1, wherein at least one of said first and second layers of conductive material comprises a coating of conductive material directly on said inner surface of the sensor cover.

6. A method of manufacturing a proximity sensor comprising: providing a cover, an emitter electrode and means for generating an electric field from said emitter electrode, wherein the emitter electrode is at least substantially enclosed by the cover, the method further comprising forming a sense electrode by providing a first layer of conductive material directly on an inner surface of said cover, wherein said step of forming said sense electrode comprises spraying the first layer of conductive material onto said inner surface of the cover and further comprising mounting a carrier plate, wherein the carrier plate is at least substantially enclosed by the cover at a distance from the sense electrode, and connecting an active guard electrode on a surface of the carrier plate facing the cover and the sense electrode.

7. A method according to claim 6, wherein said step of providing said emitter electrode comprises forming a second layer of conductive material directly on said inner surface of said cover.

8. A method according to claim 7, wherein said step of providing said emitter electrode comprises spraying said second layer of conductive material directly on said inner surface of said cover.

9. A method according to claim 6, further comprising the carrier plate being mounted at a distance from the emitter electrode.

10. A method according to claim 9, further comprising connecting a grounded shield member on said surface of said carrier plate facing the cover and the emitter electrode.

11. A method according to claim 9, further comprising connecting a grounding shield to the carrier plate on a surface opposite to said surface having said active guard electrode.

12. A method according to claim 9, further comprising positioning the cover along a movable arm of an x-ray device.

13. An X-ray imaging system, comprising:
a moveable arm having a radiation source and a radiation detector;
a housing; and
one or more proximity sensors positioned in the housing and comprising an emitter electrode, a sense electrode and electric field generator for generating an electric field from said emitter electrode to said sense electrode, wherein said sense electrode comprises a first layer of conductive material provided directly on an inner surface of a cover, wherein a carrier plate is mounted at a distance from the sense electrode, wherein the carrier plate is at least substantially enclosed by the cover, and wherein an active guard electrode is provided in respect of the sense electrode on a surface of the carrier plate facing the cover and the sense electrode.

14. An X-ray imaging system according to claim 13, wherein said emitter electrode comprises a second layer of conductive material provided directly on the cover.

15. An X-ray imaging system according to claim 14, wherein at least one of said first and second layers of conductive material comprises a layer of conductive adhesive material tape.

16. An X-ray imaging system according to claim 14, wherein at least one of said first and second layers of conductive material comprises a conductive material which is sprayed directly on said inner surface of the cover.

17. An X-ray imaging system according to claim 14, wherein at least one of said first and second layers of conductive material comprises a coating of conductive material directly on said inner surface of the cover.

18. An X-ray imaging system according to claim 13, wherein a grounded shield member is provided in respect of the emitter electrode on said surface of said carrier plate facing the cover.

19. An X-ray imaging system according to claim 13, wherein a grounding shield is connected to the carrier plate on a surface opposite to said surface having said active guard electrode.

* * * * *